US00PP32870P2

(12) United States Plant Patent
Heuger

(10) Patent No.: US PP32,870 P2
(45) Date of Patent: Mar. 2, 2021

(54) ***HELLEBORUS* PLANT NAMED 'COSEH 7900'**

(50) Latin Name: ***Helleborus* x *ericsmithii* X *Helleborus* x *hybridus***
Varietal Denomination: COSEH 7900

(71) Applicant: Josef Heuger, Glandorf (DE)

(72) Inventor: Josef Heuger, Glandorf (DE)

( * ) Notice: Subject to any disclaimer, the term of this patent is extended or adjusted under 35 U.S.C. 154(b) by 0 days.

(21) Appl. No.: 16/873,651

(22) Filed: May 27, 2020

(51) Int. Cl.
*A01H 6/72* (2018.01)
*A01H 5/02* (2018.01)

(52) U.S. Cl.
USPC ..... Plt./439

(58) Field of Classification Search
USPC ..... Plt./439
See application file for complete search history.

(56) References Cited

PUBLICATIONS

PLUTO Plant Variety Database Sep. 15, 2020.*

* cited by examiner

*Primary Examiner* — Annette H Para
(74) *Attorney, Agent, or Firm* — C. Anne Whealy

(57) ABSTRACT

A new and distinct cultivar of *Helleborus* plant named 'COSEH 7900', characterized by its upright to outwardly spreading and mounded plant habit; moderately vigorous to vigorous growth habit; dark green-colored leaves; freely flowering habit; greyed purple-colored flowers; and good garden performance.

2 Drawing Sheets

Figure 1:
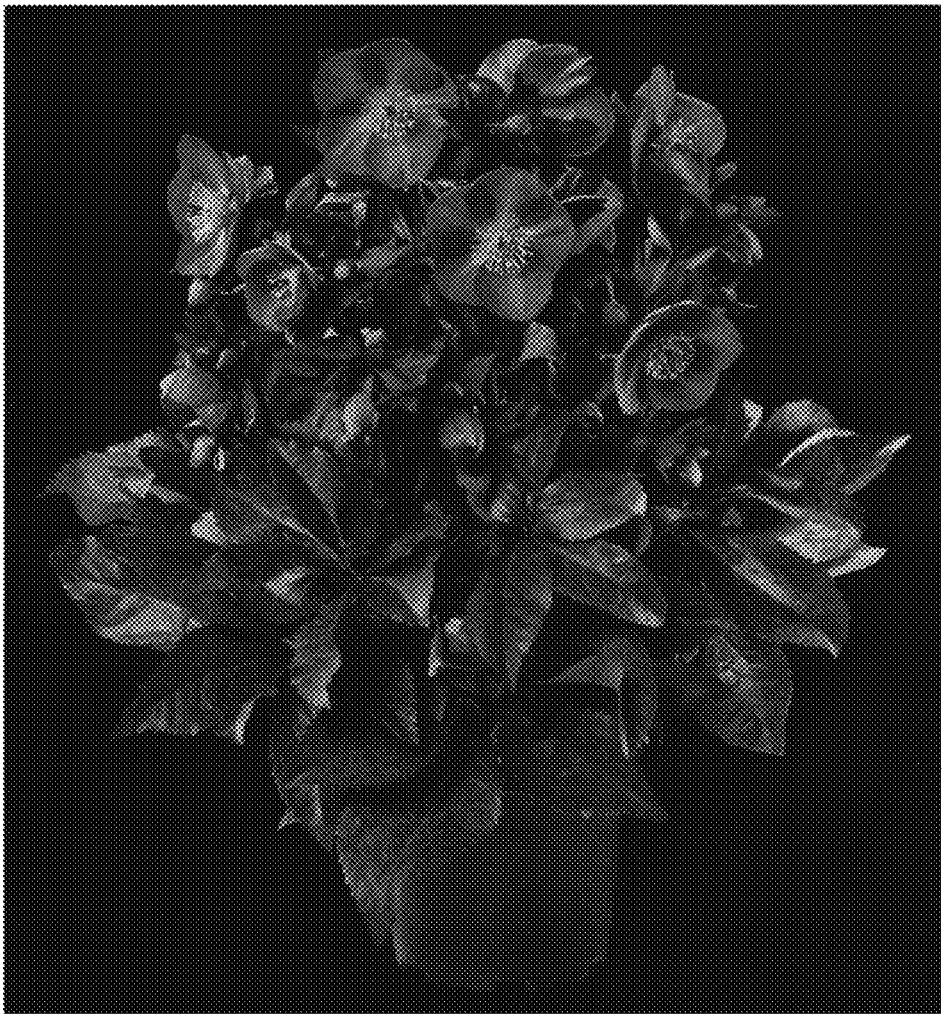

Botanical designation: *Helleborus* x *ericsmithii* X *Helleborus* x *hybridus*.
Cultivar denomination: 'COSEH 7900'.

CROSS-REFERENCED TO CLOSELY-RELATED APPLICATIONS

Title: *Helleborus* Plant Named 'COSEH 6000'
Inventor/Applicant: Josef Heuger
Plant patent application Ser. No. 16/873,648
Title: *Helleborus* Plant Named 'COSEH 6100'
Inventor/Applicant: Josef Heuger
Plant patent application Ser. No. 16/873,647
Title: *Helleborus* Plant Named 'COSEH 6300'
Inventor/Applicant: Josef Heuger
Plant patent application Ser. No. 16/873,646
Title: *Helleborus* Plant Named 'COSEH 8000'
Inventor/Applicant: Josef Heuger
Plant patent application Ser. No. 16/873,650

STATEMENT REGARDING PRIOR DISCLOSURES BY INVENTOR/APPLICANT

An European Community Plant Breeder's Rights application for the instant plant was filed by the Inventor/Applicant, Mr. Josef Heuger of Glandorf, Germany, on Jun. 6, 2019, application number 2019/1393. Foreign priority is not claimed to this application.

The Inventor/Applicant asserts that no publications nor advertisements relating to sales, offers for sale or public distribution occurred more than one year prior to the effective filing date of this application. Any information about the claimed plant would have been obtained from a direct or indirect disclosure from the Inventor or Applicant. Inventor/Applicant claims a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Helleborus* plant, botanically known as *Helleborus* x *ericsmithii* X *Helleborus* x *hybridus* and hereinafter referred to by the name 'COSEH 7900'.

The new *Helleborus* plant is a product of a planned breeding program conducted by the Inventor in Glandorf, Germany. The objective of the breeding program was to create new uniform *Helleborus* plants with unique and attractive plant habit, leaf and flower coloration and tolerance to biotic and abiotic stress.

The new *Helleborus* plant originated from a cross-pollination conducted by the Inventor in Glandorf, Germany in November, 2011 of a proprietary selection of *Helleborus* x *ericsmithii* identified as code number P840, not patented, as the female, or seed patent and an unnamed selection of *Helleborus* x *hybridus*, not patented, as the male, or pollen parent. The new *Helleborus* plant was discovered and selected by the Inventor as a single flowering plant from within the progeny of the stated cross-pollination grown in a controlled greenhouse environment in Glandorf, Germany in December, 2013.

Asexual reproduction of the new *Helleborus* plant by in vitro axillary meristem culture in a controlled environment in Glandorf, Germany since March, 2014 has shown that the unique features of this new *Helleborus* plant are stable and reproduced true to type in successive generations.

SUMMARY OF THE INVENTION

Plants of the new *Helleborus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'COSEH 7900'. These characteristics in combination distinguish 'COSEH 7900' as a new and distinct *Helleborus* plant:

1. Upright to outwardly spreading and mounded plant habit.
2. Moderately vigorous to vigorous growth habit.
3. Dark green-colored leaves.
4. Freely flowering habit.
5. Greyed purple-colored flowers.
6. Good garden performance.

Plants of the new *Helleborus* differ from plants of the female parent selection in the following characteristics:

1. Plants of the new *Helleborus* are more vigorous than plants of the female parent selection.
2. Plants of the new *Helleborus* flower earlier than plants of the female parent selection.

Plants of the new *Helleborus* differ from plants of the male parent selection in the following characteristics:

1. Plants of the new *Helleborus* are more vigorous than plants of the male parent selection.
2. Flowers of plants of the new *Helleborus* are greyed purple in color whereas flowers of plants of the male parent selection are reddish in color.

Plants of the new *Helleborus* can be compared to plants of *Helleborus* x *ericsmithii* X *Helleborus* x *hybridus* 'COSEH 6000', disclosed in a U.S. Plant Patent application filed concurrently. Plants of the new *Helleborus* differ primarily from plants of 'COSEH 6000' in flower color as flowers of plants of the new *Helleborus* are lighter greyed purple in color than flowers of plants of 'COSEH 6000'.

Plants of the new *Helleborus* can be compared to plants of *Helleborus* x *ericsmithii* X *Helleborus* x *hybridus* 'COSEH 6100', disclosed in a U.S. Plant Patent application filed concurrently. Plants of the new *Helleborus* differ primarily from plants of 'COSEH 6100' in flower color as plants of the new *Helleborus* have greyed purple-colored flowers whereas plants of 'COSEH 6100' have greyed purple to greyed red purple-colored flowers.

Plants of the new *Helleborus* can be compared to plants of *Helleborus* x *ericsmithii* X *Helleborus* x *hybridus* 'COSEH 6300', disclosed in a U.S. Plant Patent application filed concurrently. Plants of the new *Helleborus* differ primarily from plants of 'COSEH 6300' in flower color as plants of the new *Helleborus* have greyed purple-colored flowers whereas plants of 'COSEH 6300' have yellow green and green white-colored flowers with red purple to greyed purple-colored margins.

Plants of the new *Helleborus* can be compared to plants of *Helleborus* x *ericsmithii* X *Helleborus* x *hybridus* 'COSEH 8000', disclosed in a U.S. Plant Patent application filed concurrently. Plants of the new *Helleborus* differ primarily from plants of 'COSEH 8000' in flower color as plants of the new *Helleborus* have greyed purple-colored flowers whereas plants of 'COSEH 8000' have greyed purple to dark purple-colored flowers.

Plants of the new *Helleborus* can also be compared to plants of *Helleborus* x *ericsmithii* X *Helleborus* x *hybridus* 'COSEH 4600', disclosed in U.S. Plant Pat. No. 30,488. In side-by-side comparisons, plants of the new *Helleborus* differ primarily from plants of 'COSEH 4600' in the following characteristics:

1. Plants of the new *Helleborus* are more vigorous and taller than plants of 'COSEH 4600'.
2. Plants of the new *Helleborus* differ from plants of 'COSEH 4600' in flower color as plants of the new *Helleborus* have greyed purple to dark purple-colored flowers whereas plants of 'COSEH 4600' have dark greyed purple-colored flowers.

BRIEF DESCRIPTION OF THE PHOTOGRAPHS

The accompanying colored photographs illustrate the overall appearance of the new *Helleborus* plant showing the colors as true as it is reasonably possible to obtain in colored reproductions of this type. Colors in the photographs may differ slightly from the color values cited in the detailed botanical description which accurately describe the colors of the new *Helleborus* plant.

The photograph on the first sheet (FIG. 1 of 2) is a side perspective view of a typical flowering plant of 'COSEH 7900' grown in a container.

Figure 2:
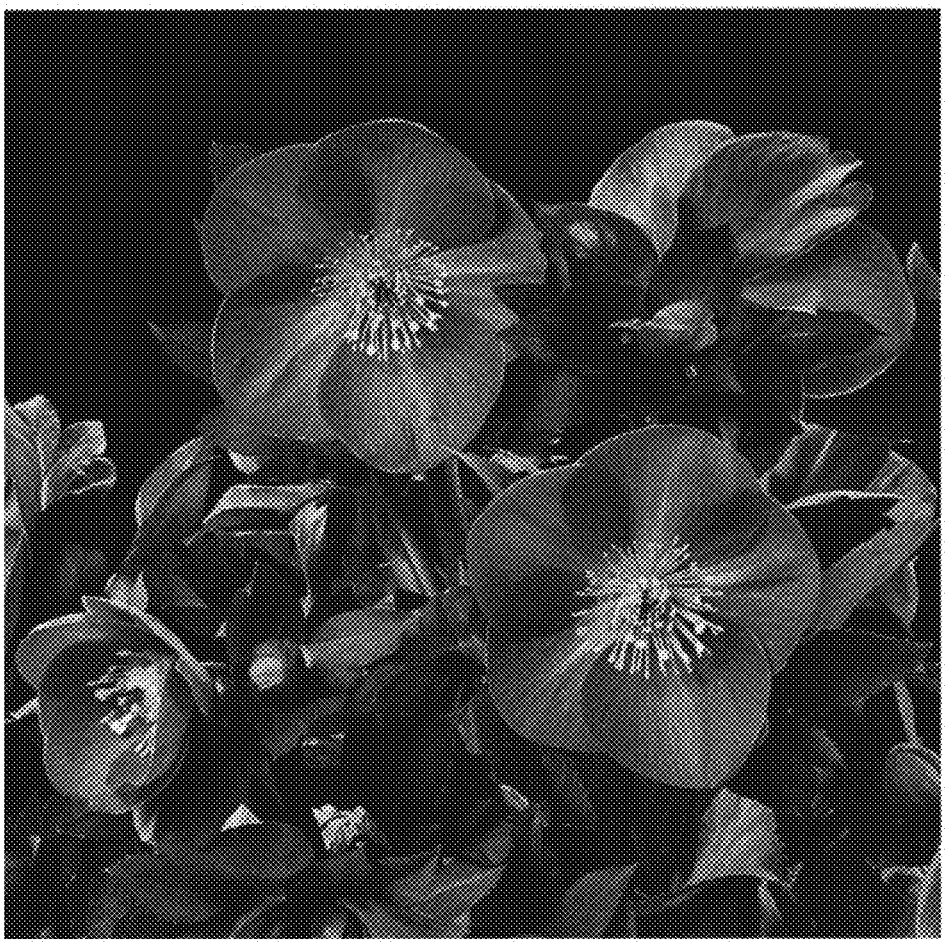

The photograph on the second sheet (FIG. 2 of 2) is a close-up view of a typical flowering plant of 'COSEH 7900'.

DETAILED BOTANICAL DESCRIPTION

The aforementioned photographs and following observations, measurements and values describe plants grown during March in 17-cm containers in a glass-covered greenhouse in Glandorf, Germany and under cultural practices typical of commercial *Helleborus* production. During the production of the plants, day temperatures ranged from 12° C. to 32° C. and night temperatures ranged from 5° C. to 12° C. Plants were four months old when the photographs and the description were taken. In the following description, color references are made to The Royal Horticultural Society Colour Chart, 2015 Edition, except where general terms of ordinary dictionary significance are used.

Botanical classification: *Helleborus* x *ericsmithii* X *Helleborus* x *hybridus* 'COSEH 7900'.

Parentage:

*Female, or seed, parent.*—Proprietary selection of *Helleborus* x *ericsmithii* disclosed as code number P840, not patented.

*Male, or pollen, parent.*—Unnamed selection of *Helleborus* x *hybridus*, not patented.

Propagation:

*Type.*—In vitro axillary meristem culture.

*Time to initiate roots, winter.*—About 55 days at temperatures about 12° C.

*Time to produce a rooted young plant, winter.*—About 170 days at temperatures ranging from 4° C. to 15° C.

*Root description.*—Thick to thin, fleshy; typically white to brown in color, actual color of the roots is dependent on substrate composition, water quality, fertilizer type and formulation, substrate temperature and physiological age of roots.

*Rooting habit.*—Low branching; sparse.

Plant description:

*Plant and growth habit.*—Herbaceous perennial; upright to outwardly spreading and mounding plant habit with flowers held within and above the foliar plane; plant shape, flattened globular; moderately vigorous to vigorous growth habit and moderate to rapid growth rate.

*Plant height, soil level to top of foliar plane*.—About 28.4 cm.

*Plant height, soil level to top of flowers*.—About 48.4 cm.

*Plant diameter* (*area of spread*).—About 74 cm.

Leaf description:

*Arrangement*.—Leaves arranged in a basal rosette; leaves palmately compound with typically five leaflets per leaf.

*Leaf length*.—About 20.6 cm.

*Leaf width*.—About 24.3 cm.

*Leaflet length*.—About 15 cm.

*Leaflet width*.—About 6.5 cm.

*Leaf shape*.—Palmate; reniform in outline.

*Leaflet shape*.—Elliptic to narrowly elliptic or narrowly ovate; lower leaves are occasionally cleft.

*Leaflet apex*.—Acute.

*Leaflet base*.—Attenuate.

*Leaflet margin*.—Serrate; coarsely undulate.

*Leaflet texture and luster, upper surface*.—Smooth, glabrous; leathery; moderately glossy.

*Leaflet texture and luster, lower surface*.—Smooth, glabrous; leathery; slightly glossy.

*Leaflet venation pattern*.—Pinnate.

*Leaflet color*.—Developing leaflets, upper surface: Close to between 143A and 146A; midvein proximally tinged with close to 177A to 177B. Developing leaflets, lower surface: Close to 148A strongly tinged with close to 197A. Fully developed leaflets, upper surface: Slightly darker than between 139A and 147A; venation, close to 144A and towards the base, close to N186C. Fully developed leaflets, lower surface: Close to between 147B and 148B; venation, close to 187A.

*Petioles*.—Length: About 19.3 cm. Diameter: About 6 mm to 8 mm. Strength: Strong. Texture and luster, upper and lower surfaces: Smooth, glabrous; moderately glossy. Color, upper surface: Close to 144A to 144B heavily covered with fine dots, close to between 183A and N186C. Color, lower surface: Close to 144A to 144B heavily covered with fine dots, close to between 183A and N186C and proximally, closer to N186C.

Flower description:

*Flower shape and habit*.—Rotate flowers; flowers moderately cupped; arranged in panicles; freely flowering habit with about five flowers per inflorescence and about 50 flowers developing per plant; flowers face mostly outwardly to slightly nodding.

*Fragrance*.—None detected.

*Natural flowering season*.—Plants begin flowering about ten months after planting; plants flower naturally from winter into the late winter in Germany.

*Flower longevity on the plant*.—About ten days; sepals persistent, other flower parts are not persistent.

*Flower buds*.—Length: About 1.8 cm. Diameter: About 1.2 cm. Shape: Broadly ovate. Texture and luster: Smooth, glabrous; slightly glossy. Color: Close to 145C distally tinged with close to 186C and proximally, close to 186A.

*Inflorescence height* (*including peduncle*).—About 49.4 cm.

*Inflorescence diameter*.—About 14.9 cm.

*Flower diameter*.—About 6.9 cm by 6.9 cm.

*Flower depth* (*height*).—About 2.2 cm.

*Petals*.—All petals are transformed into nectaries.

*Sepals*.—Quantity and arrangement: About five, arranged in a single whorl. Length: About 3.7 cm. Width: About 3.6 cm. Shape: Broadly ovate, slightly concave. Apex: Obtuse. Base: Truncate to broadly cuneate. Margin: Entire; slightly undulate. Texture and luster, upper surface: Smooth, glabrous; matte. Texture and luster, lower surface: Smooth, glabrous; slightly glossy. Color: When opening, upper surface: Close to between 155A and 158D; towards the margins and apex, close to 186D. When opening, lower surface: Close to between 145D and 150D; towards the margins and apex, close to 186C to 186D; towards the base, flushed with close to 184B. Fully opened, upper surface: Ground color, close to 155A; towards the margins, close to 185D; towards the apex, close to 186B; with development, color becoming closer to between N186C and N187A; venation, close to 155A or similar to lamina. Fully opened, lower surface: Close to 145B; towards the margins, close to 182C; towards the apex, close to 185D; with development, color becoming closer to between N186C and N187A; venation, close to 155A or similar to lamina.

*Flower bracts*.—Quantity per flower: Typically one or two. Length: About 7 cm. Width: About 5.1 cm. Shape: Ovate to tri-lobed. Apex: Acute. Base: Truncate. Margin: Sparsely and finely serrate. Color, upper surface: Close to between 147A and N189A; midvein, close to 187A. Color, lower surface: Close to between 148A and 197A; venation, close to N186C.

*Peduncles*.—Length: About 40.1 cm. Diameter: About 9 mm. Aspect: About 20° from vertical. Strength: Strong, bending with the weight of the flowers. Texture and luster: Smooth, glabrous; moderately glossy. Color: Close to 150D, heavily covered with fine dots, close to 187B.

*Pedicels*.—Length: About 3.6 cm. Diameter: About 2 mm. Aspect: About 10° to 25° from peduncle axis. Strength: Moderately strong. Texture and luster: Smooth, glabrous; moderately glossy. Color: Close to 182C.

*Reproductive organs*.—Stamens: Quantity per flower: About 70. Filament length: About 1.6 cm. Filament color: Close to NN155D. Anther shape: Double and broadly reniform; basifixed. Anther size: About 1.5 mm by 2.5 mm. Anther color: Close to 150D. Pollen amount: Sparse to moderate. Pollen color: Close to 4D to lighter than 4D. Pistils: Quantity per flower: About three to six. Pistil length: About 1.4 cm. Stigma diameter: About 0.3 mm. Stigma shape: Club-shaped. Stigma color: Close to NN155A. Style length: About 1.3 cm. Style color: Close to 186B to 186C. Ovary color: Close to 150D. Nectaries (transformed petals): Quantity per flower: About eleven. Length: About 1.1 cm. Diameter: About 4 mm. Shape: Tubular, flattened. Texture and luster, inner and outer surfaces: Smooth, glabrous; slightly glossy. Color, immature, inner surface: Close to 150B. Color, immature, outer surface: Close to 150B; spot at base, close to 151A to 151B. Color, mature, inner surface: Close to 151B; with development, becoming closer to 151A and towards the apex, close to 153C; venation, similar to lamina. Color, mature, outer surface: Close to 151B; spot at base, close to 151A; with development, becoming closer to 151A, towards the apex, close to 153A and spot, closer to 153A; venation, similar to lamina.

*Seeds and fruits*.—To date, seed and fruit development have not been observed on plants of the new *Helleborus*.

Garden performance: Plants of the new *Helleborus* have been observed to have good garden performance and to tolerate rain, wind, high temperatures about 35° C. and to be suitable for USDA Hardiness Zones 5 through 9.

Pathogen & pest resistance: To date, plants of the new *Helleborus* have not been observed to be resistant to pathogens and pests common to *Helleborus* plants.

It is claimed:

1. A new and distinct *Helleborus* plant named 'COSEH 7900' as illustrated and described.

* * * * *